United States Patent [19]
Nijkamp et al.

[11] Patent Number: 5,829,381
[45] Date of Patent: Nov. 3, 1998

[54] DEVICE FOR MEASURING THE COMPLEX IMPEDANCE OF MILK, AND PULSATOR HAVING SUCH A DEVICE

[75] Inventors: Jan Marinus Nijkamp; Berend Andries Posthuma, both of Emmeloord, Netherlands

[73] Assignee: Gascoigne-Melotte B.V., Emmeloord, Netherlands

[21] Appl. No.: 676,142
[22] PCT Filed: Feb. 8, 1995
[86] PCT No.: PCT/NL95/00047
  § 371 Date: Jul. 16, 1996
  § 102(e) Date: Jul. 16, 1996
[87] PCT Pub. No.: WO95/22888
  PCT Pub. Date: Aug. 31, 1995

[30] Foreign Application Priority Data

Feb. 28, 1994 [NL] Netherlands ............................ 9400305

[51] Int. Cl.$^6$ .................................................... A01J 5/00
[52] U.S. Cl. ................................. 119/14.55; 119/14.54
[58] Field of Search ......................... 119/14.54, 14.55; 73/304 R

[56] References Cited

U.S. PATENT DOCUMENTS

| | | | |
|---|---|---|---|
| 4,403,568 | 9/1983 | Fukuhara et al. | 119/14.14 |
| 5,590,622 | 1/1997 | Wilson et al. | 119/14.54 |
| 5,651,329 | 7/1997 | Van Den Burg et al. | 119/14.02 |

FOREIGN PATENT DOCUMENTS

| | | |
|---|---|---|
| 0 137 367 | 4/1985 | European Pat. Off. . |
| 8 301 231 | 11/1984 | Netherlands . |
| 1160900 | 8/1969 | United Kingdom . |
| 2 257 008 | 1/1993 | United Kingdom . |

*Primary Examiner*—Edgar S. Burr
*Assistant Examiner*—Dave A. Ghatt
*Attorney, Agent, or Firm*—Young & Thompson

[57] ABSTRACT

A device for measuring the complex impedance, such as the electrical conductance and/or the capacitance, of milk, for example in connection with mastitis detection, comprises a sample chamber which is provided with sensors and in which a milk sample can be received. The sensors are mounted in the sample chamber at an essentially mutually equal height level. The sensors may also have an elongated shape and be mutually parallel.

8 Claims, 1 Drawing Sheet

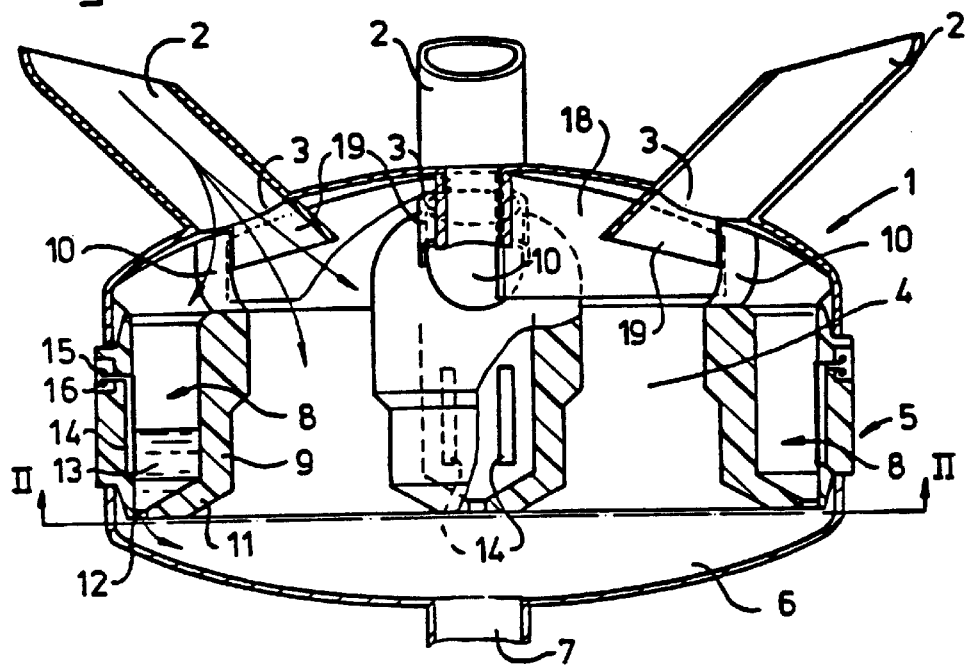
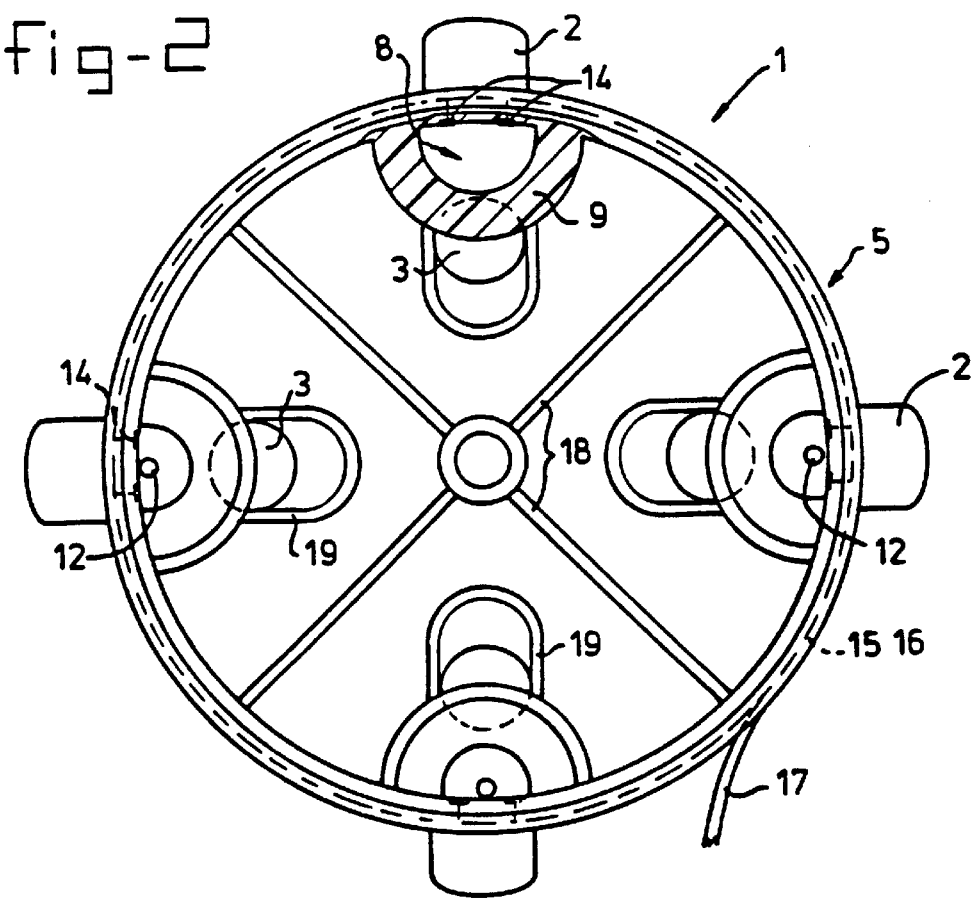

DEVICE FOR MEASURING THE COMPLEX IMPEDANCE OF MILK, AND PULSATOR HAVING SUCH A DEVICE

The invention relates to the field of measuring the complex impedance, such as the electrical conductance and/or the capacitance, of milk, for example for detecting mastitis in dairy animals. In that connection, it is known to use, in a milking installation, a detection device which has a sample chamber in which a milk sample can be received. The sample chamber is generally so designed that the milk sample received therein stays relatively stationary for some time so that the conductance of the milk can be measured by means of the sensors.

EP-B-137 367 discloses some embodiments of such a sample chamber. Thus, the short milk hose between the teat cup and the pulsator may be provided, over a section of its length, with an insulated channel which opens out again via a small opening into the main channel. Two electrodes are mounted in the insulated channel.

As an alternative, it is also known to constrict the milk hose locally so that a stagnation point occurs in the milk flow. Mounted just in front of the constriction are the electrodes which measure the conductance of the relatively slowly flowing milk.

It is furthermore known, to provide, in the pulsator itself, sample chambers in which the electrodes are sited.

In all these known detection devices, however, the problem arises that the measurements of the impedance obtained are inaccurate. The consequence of this is that said measurements are not reliable enough and cannot provide any clear information relating to the presence or absence of mastitis. The object of the invention is therefore to provide such a device which will in fact yield reliable results.

That object is achieved in that the sensors are mounted in the sample chamber at an essentially mutually equal height level. At the same time, the reliability can be increased still further if the sensors have an elongated shape and are mutually parallel. If the elongated sensors are, in addition, transverse to the milk surface within a certain angular range, for example between 0° and ±45°, fluctuations in the flow rate of the milk sample do not have any influence on the measuring accuracy. An elongated shape must be understood as meaning any shape in which a clear longitudinal direction can be distinguished, such as a rectangle, oval, exclamation mark etc.

Such fluctuations in the flow rate of the milk sample in the sample chamber are the consequence of the pulsating nature of the milk flow and the varying rate at which the animals deliver their milk; with such an arrangement and design of the sensors, however, they have hardly any influence on the measurements, as a result of which a very constant, reliable picture is obtained.

As already discussed above, such a sample chamber ban be received in the short milk hose itself. Preferably, however, such a measuring device is provided in a pulsator for a milking installation. The pulsator disclosed in EP-B-137 367 contains, in a known manner, a collecting space having a lid which has feed openings which may each be connected to a teat cup of the milking device, in which collecting space sample chambers are separated off for receiving a milk sample originating from an associated teat cup, which sample chambers are each provided with sensors for measuring the complex impedance of the milk.

In such a pulsator, an important improvement in the measurements can be obtained if the sensors are situated next to one another when viewed in the circumferential direction of the collecting space. In this arrangement, the sensors are situated at equal levels when viewed in the vertical direction. In this case, too, the influence of fluctuations in the milk supply can largely be eliminated if the sensors have an elongated shape, and the longitudinal direction of the sensors is directed perpendicularly to the circumferential direction of the collecting space.

Each sample chamber can be designed so that it is bounded, on the one hand, by a chamber wall extending into the collecting space from the circumferential wall and, on the other hand, by the adjacent part of the circumferential wall.

If said chamber wall terminates at some distance below the associated feed opening, the main flow of the milk squirts along the sample chamber directly into the collecting space. Only a fraction of the total flow enters the sample chamber, for example dropwise, as a result of which a milk sample can collect therein which stays relatively stationary. In such a state, accurate measurements can be made.

The chamber wall is sealed off at the bottom with respect to the circumferential wall and is provided with a drainage opening. The milk slowly flows back out of the sample chamber via the opening so that a fresh milk sample can always be measured.

In order to prevent measurements of one milk sample originating from one teat cup being disturbed as a consequence of the entry of milk from another teat cup, the lid is provided, on its inside, with partitions which extend radially up to the area between two openings. The partitions hold back even the finest milk drops so that each sample chamber receives only milk from the associated teat cup. A reliable measurement is thus ensured also for each quarter.

As an alternative, an approximately semicylindrical wall whose open side is directed towards the circumferential wall may be provided around each opening.

An exemplary embodiment of a pulsator according to the invention will be explained in greater detail below by reference to the figures.

FIG. 1 shows a side view in cross section of a pulsator according to the invention.

FIG. 2 shows a bottom view of the pulsator according to FIG. 1.

The pulsator shown in FIG. 1 comprises, in a known manner, a lid 1 which carries four feed pipe pieces 2 (of which only three are visible in FIG. 1). Each pipe piece is connected via opening 3 in the lid to the interior of the pulsator, designated as collecting space 4.

The lid is attached to the circumferential wall 5, which is sealed at its bottom by base 6. Said base 6 furthermore carries a drainage pipe 7, via which the milk is drained into a milking installation.

Each feed pipe piece 2 is connected in a known manner to a flexible short milk hose which is not shown in further detail and is connected to a teat cup, which is also not shown.

Mounted underneath each feed opening 3 in the collecting space 4 is a so-called sample chamber 8. Each sample chamber 8 is bounded by an essentially semicylindrical chamber wall 9 and the adjacent section of the circumferential wall 5. At the top, the chamber wall 9 has a cutout 10, via which a portion of the milk which flows into the collecting space 4 through the feed pipe piece 2 enters the sample chamber 8. The main flow of the milk supply is directed straight into the collecting space 4, which means that only a small part of the milk enters said sample chamber 8, for example dropwise.

The chamber wall 9 is connected at the bottom to the circumferential wall 5 by means of a base wall 11. In said base wall there is a small opening 12, via which opening 12 the milk sample 13 collecting in the sample chamber 8 slowly drains away.

According to the invention two sensors in the form of electrodes 14 are now mounted on the inside of the circumferential wall 5. The surfaces of said electrodes are in contact with the milk sample 13. Each electrode is connected to an electrical conductor 15 or 16. The conductors needed may be connected via cable 17 to a measuring device which is not shown in further detail. As already mentioned, for example, conductance and/or capacitance measurements may be involved.

As can be seen in FIG. 1, the electrodes 14 are mounted, in the operating state of the pulsator, at the same level. They furthermore have an elongated shape and are transverse to the surface of the milk sample 13 in the sample chamber 8. In practice, the pulsator may be suspended in an inclined position. Within certain limits, for example up to an inclined position of 45° with respect to the milk surface, reliable measurements can nevertheless be performed. Owing to this positioning and design of the electrodes, a reliable measurement can always nevertheless be obtained even with varying flow rate as a consequence of severe fluctuations in the height of the milk surface of the milk sample 13. After all, it is always ensured that both electrodes are in contact with the milk; in addition, placing the sample chamber in a relatively quiet region of the collecting space 4 ensures that the milk sample 13 stays relatively stationary. In addition, the milk sample 13 stays in the sample chamber 8 for a relatively long time, since the milk can drain away only slowly through the drainage opening 12. All these measures contribute to the accuracy of the measurement result obtained.

Four partitions 18 are furthermore mounted in the lid 1. Each partition 18 extends from the centre of the lid to the circumferential wall 5 and runs between two feed openings 3. Said partitions 18 ensure that only milk from the feed opening 3 situated directly above it enters each sample chamber 8. It is thus possible to detect reliably which teat of the animal being milked is suffering from mastitis. In addition to, or instead of, said partitions 18, an approximately semicylindrical wall 19 can be mounted at each opening 3.

A sensor for measuring the milk temperature, which is a good indication of the body temperature of the animal, can be mounted in one of the sample chambers 8.

We claim:

1. Milking claw piece for an installation for milking animals, provided with a collecting space having a lid which has feed openings for connection to a teat cup, and comprising sample chambers separated from said collecting space for receiving a milk sample originating from an associated teat cup, which sample chambers are each provided with a pair of sensors for measuring the complex impedance, such as the electrical conductance and/or the capacitance, of milk, wherein the sensors of each pair have an identical elongated shape, are mutually parallel and are mounted at an equal level vertically of the collecting space.

2. Milking claw piece according to claim 1, wherein the sensors are received peripherally of the collecting space.

3. Milking claw piece according to claim 1, wherein the lid is provided, on its inside, with partitions which extend radially up to the area between two openings.

4. Milking claw piece according to claim 1, wherein there is provided, around each opening, an approximately semicylindrical wall whose open side is directed towards the circumferential wall.

5. Milking claw piece according to claim 1, wherein each sample chamber is bounded, on the one hand, by a chamber wall extending into the collecting space from a circumferential wall of said claw piece and, on the other hand, by an adjacent part of the circumferential wall.

6. Milking claw piece according to claim 5, wherein each sample chamber terminates at some distance below an overlying feed opening.

7. Milking claw piece according to claim 5, wherein the chamber wall is essentially semicylindrical.

8. Milking claw piece according to claim 5, wherein the chamber wall is sealed off at the bottom against the circumferential wall and is provided with a drainage opening.

* * * * *